US012766175B2

(12) United States Patent
Fang et al.

(10) Patent No.: US 12,766,175 B2
(45) Date of Patent: Oct. 20, 2026

(54) *BIFIDOBACTERIUM LONGUM* **SUBSP. *INFANTIS* FOR ALLEVIATING PARKINSON'S DISEASE AND USE THEREOF**

(71) Applicant: WECARE PROBIOTICS CO., LTD., Jiangsu (CN)

(72) Inventors: Shuguang Fang, Jiangsu (CN); Yao Dong, Jiangsu (CN); Yixuan Fan, Jiangsu (CN); Zhonghui Gai, Jiangsu (CN); Jianguo Zhu, Jiangsu (CN)

(73) Assignee: WECARE PROBIOTICS CO., LTD., Suzhou (CN)

( * ) Notice: Subject to any disclaimer, the term of this patent is extended or adjusted under 35 U.S.C. 154(b) by 0 days.

(21) Appl. No.: 18/995,578

(22) PCT Filed: May 27, 2024

(86) PCT No.: PCT/CN2024/095474

§ 371 (c)(1),
(2) Date: Jan. 16, 2025

(87) PCT Pub. No.: WO2025/030991

PCT Pub. Date: Feb. 13, 2025

(65) Prior Publication Data

US 2026/0108568 A1 Apr. 23, 2026

(30) Foreign Application Priority Data

Aug. 9, 2023 (CN) ......................... 202310994244.5

(51) Int. Cl.

| | |
|---|---|
| ***A61K 35/745*** | (2015.01) |
| ***A61K 35/00*** | (2006.01) |
| ***A61P 25/16*** | (2006.01) |
| ***C12N 1/205*** | (2026.01) |
| ***C12R 1/01*** | (2006.01) |

(52) U.S. Cl.

CPC ............ *A61K 35/745* (2013.01); *A61P 25/16* (2018.01); *C12N 1/205* (2021.05); *A61K 2035/115* (2013.01); *C12R 2001/01* (2021.05)

(58) Field of Classification Search

CPC . A61K 35/745; A61K 2035/115; A61P 25/16; C12N 1/205; C12R 1/01
See application file for complete search history.

(56) References Cited

FOREIGN PATENT DOCUMENTS

| | | | |
|---|---|---|---|
| CN | 109055269 | A | 12/2018 |
| CN | 111971056 | A | 11/2020 |
| CN | 115887504 | A | 4/2023 |
| CN | 116509902 | A | 8/2023 |
| CN | 116751727 | A | 9/2023 |
| WO | 2017/130859 | A1 | 8/2017 |

OTHER PUBLICATIONS

Chinese Patent Office, Official Action for Application No. 202310994244.5, Sep. 20, 2023.
Chinese Patent Office, International Search Report for PCT/CN2024/095474, Aug. 2, 2024.
Park, et al., "Effect of probiotic supplementation on gastrointestinal motility, inflammation, motor, non-motor symptoms and mental health in Parkinson's disease: a meta-analysis of randomized controlled trials" Gut Pathogens (2023) 15:9.

*Primary Examiner* — Robert A Zeman
(74) *Attorney, Agent, or Firm* — Robert C. Netter, Jr.; Dann, Dorfman, Herrell & Skillman

(57) ABSTRACT

Provided are a *Bifidobacterium longum* subsp. *infantis* for alleviating Parkinson's disease and a use thereof, and the *Bifidobacterium longum* subsp. *infantis* for alleviating Parkinson's disease is named as *Bifidobacterium longum* subsp. *infantis* BI03 strain, with a deposit number of CGMCC No. 24473 and deposit date of Mar. 7, 2022. The strain can significantly alleviate the symptoms of Parkinson's disease, specifically manifested in: alleviating Parkinson's disease-related dyskinesia and corticosterone elevation; weakening the neuroinflammation associated with Parkinson's disease; promoting glutathione and weakening brain oxidative stress damage.

5 Claims, 7 Drawing Sheets

Specification includes a Sequence Listing.

*BIFIDOBACTERIUM LONGUM* SUBSP. *INFANTIS* FOR ALLEVIATING PARKINSON'S DISEASE AND USE THEREOF

This application is a § 371 application of PCT/CN2024/095474, filed May 27, 2024, which claims priority to Chinese Patent Application No. 202310994244.5, filed on Aug. 9, 2023. The foregoing applications are incorporated by reference herein.

Incorporated herein by reference in its entirety is the Sequence Listing being concurrently submitted as a XML file named SeqList, created Jan. 16, 2025, and having a size of 5,004 bytes.

TECHNICAL FIELD

The present application belongs to the technical field of microbial cultivation, relates to a *Bifidobacterium longum* subsp. *infantis* for alleviating Parkinson's disease and a use thereof, and in particular to a *Bifidobacterium longum* subsp. *infantis* BI03 strain, a probiotic preparation containing the same, and a use in the preparation of a drug or a health product for preventing, alleviating or treating Parkinson's disease thereof.

BACKGROUND

Parkinson's disease is a chronic progressive neurological disorder mainly characterized by hand tremors, muscle stiffness, and bradykinesia, all these symptoms are associated with reduced dopamine levels in the brain. Although a variety of drugs have been developed to relieve the symptoms of Parkinson's disease, many patients are unsatisfied with the existing treatments and long-term use of certain drugs can lead to side effects and drug resistance problems. Therefore, finding new treatment schemes and preventing the occurrence and progression of Parkinson's disease have become very important. In recent years, probiotics have attracted widespread attention in the field of Parkinson's disease as a potential treatment option.

Some studies have shown that probiotics may have antioxidant and neuroprotective effects that can alleviate Parkinson's disease-related symptoms by affecting the Brain-Gut Axis. The gut microbial community is one of the key factors influencing the Brain-Gut Axis. Probiotics can regulate the Brain-Gut Axis communication by affecting the substances in the gut such as metabolites, neurotransmitters, and short-chain fatty acids, thereby alleviating Parkinson's disease-related symptoms. By ingesting probiotics, the composition and balance of the gut microbial community can be regulated to reduce damage to nervous system caused by factors such as chronic low-grade inflammation and oxidative stress. Chronic inflammation is a common feature of many neurodegenerative diseases and is closely related to the development and progression of Parkinson's disease. Some strains in probiotics can reduce the inflammatory response by suppressing inflammation response and regulating the immune system. In addition, oxidative stress is one of the causes of many neurodegenerative diseases, and certain probiotics can protect the nervous system by increasing antioxidative enzyme activity and removing free radicals.

The study of probiotic intervention in Parkinson's disease may provide new inspiration for the alleviation of Parkinson's disease-related motor defects, nerve damage, intestinal flora imbalance, etc. Probiotics can be used as potential therapeutic or additional therapeutic alternative scheme.

SUMMARY

The present application provides a *Bifidobacterium longum* subsp. *infantis* for alleviating Parkinson's disease and use thereof, in particular to a *Bifidobacterium longum* subsp. *infantis* BI03 strain, a probiotic preparation containing the same, and a use in the preparation of a drug or a health product for preventing, alleviating or treating Parkinson's disease thereof.

In a first aspect, the present application provides a *Bifidobacterium longum* subsp. *infantis* for alleviating Parkinson's disease, and the *Bifidobacterium longum* subsp. *infantis* for alleviating Parkinson's disease is named as *Bifidobacterium longum* subsp. *infantis* BI03 strain and was deposited on Mar. 7, 2022, with China General Microbiological Culture Collection Center (CGMCC), located at No. 1 Beichen West Road, Chaoyang District, Beijing 100101, P. R. China under a deposit number of CGMCC No. 24473.

In the present application, a new *Bifidobacterium longum* subsp. *infantis* for alleviating Parkinson's disease is isolated and deposited from fecal samples of healthy breastfed infants in Dali Bai Autonomous Prefecture, Yunnan Province, China, which is named as *Bifidobacterium longum* subsp. *infantis* BI03 strain. The *Bifidobacterium longum* subsp. *infantis* BI03 strain can significantly alleviate the symptoms of Parkinson's disease, specifically manifested in: (1) significantly alleviating Parkinson's disease-related dyskinesia and corticosterone elevation; (2) weakening the neuroinflammation associated with Parkinson's disease; (3) significantly promoting glutathione production and weakening brain oxidative stress damage. This discovery provides new ideas for the development of new drugs to prevent or treat Parkinson's disease. In addition, *Bifidobacterium longum* subsp. *infantis* is a probiotic, it has high safety and not easy resistant when used in the preparation of products for preventing or treating Parkinson's disease.

Steps of screening *Bifidobacterium longum* subsp. *infantis* BI03 strain involved in the present application are as follows:

(1) selecting a fecal sample of healthy breastfed infants in Dali Bai Autonomous Prefecture, Yunnan Province, China, performing 10-fold gradient dilution on the fecal sample with 0.9% normal saline for 3 times, coating on a MRS solid medium (reagents are purchased from Hope Bio), culturing at 37° C. for 48 h, picking out colonies with different morphologies and then streaking on the surface of MRS solid medium for purification, picking out single colonies and culturing with MRS liquid medium at 37° C. for expanding, and then preserving with a 30% mass concentration of glycerol.

(2) Performing in vitro physiological properties tests in view of several preserved strains, screening out a single strain with the best gastrointestinal fluid tolerance (artificial simulation), HT-29 cell adhesion ability, bacteriostatic ability and functional oligosaccharide utilization ability, and identifying and preserving the strain.

In a second aspect, the present application provides a microbial preparation for preventing, alleviating or treating Parkinson's disease, and the microbial preparation includes the *Bifidobacterium longum* subsp. *infantis* BI03 strain as described in the first aspect.

The *Bifidobacterium longum* subsp. *infantis* BI03 strain of the present application can be applied separately to related products, and can also be combined with other strains and applied in related products.

Preferably, a viable bacteria count of the *Bifidobacterium longum* subsp. *infantis* BI03 strain in the microbial preparation is not less than $1\times10^9$ CFU/mL or $1\times10^9$ CFU/g, for example, $1\times10^9$ CFU/g (CFU/mL), $5\times10^9$ CFU/g (CFU/mL), $1\times10^{10}$ CFU/g (CFU/mL), $3\times10^{10}$ CFU/g (CFU/mL), $5\times10^{10}$ CFU/g (CFU/mL), $1\times10^{11}$ CFU/g (CFU/mL), $5\times10^{11}$ CFU/g (CFU/mL), $1\times10^{12}$ CFU/g (CFU/mL), or $1\times10^{13}$ CFU/g (CFU/mL).

Preferably, the microbial preparation further includes a *Bifidobacterium longum* BL21 strain which was deposited on Jan. 27, 2015 with China General Microbiological Culture Collection Center (CGMCC), located at No. 1 Beichen West Road, Chaoyang District, Beijing 100101, P. R. China under a deposit number of CGMCC No. 10452.

The present application further creatively finds that the BI03 strain can be used in combination with the BL21 for preventing, alleviating or treating Parkinson's disease, which has a significantly excellent effect than a single strain or other compound method, indicating that the BI03 strain and the BL21 strain have a synergistic effect on the aforementioned efficacy.

Preferably, a viable bacteria count ratio of the *Bifidobacterium longum* subsp. *infantis* BI03 strain to the *Bifidobacterium longum* BL21 strain is (2-4):1, for example, 2:1, 5:2, 3:1, 7:2, or 4:1.

Based on the potential interactions between the BI03 strain and the BL21 strain in terms of the above efficacy, the two strains have a better synergistic effect when meeting the specific mass ratio relationship described above.

Preferably, a dosage form of the microbial preparation includes a lyophilized powder agent, a capsule agent, a tablet agent or a granule agent.

Preferably, the microbial preparation further includes a protectant and/or an auxiliary additive.

Preferably, the protectant is selected from any one or a combination of at least two of skimmed milk, gelatin, maltodextrin, Arabic gum, dextran, sodium algae, polyvinyl pyrrolidone, sucrose, lactose, trehalose, sorbitol or xylitol.

Preferably, the auxiliary additive is selected from any one or a combination of at least two of resistant dextrin, oligofructose, oligogalactose, oligoxylose, iso-malto-oligosaccharide, soybean oligosaccharide, inulin, *Spirulina, Arthrospira, Coriolus versicolor* polysaccharide, stachyose, polyglucose, α-lactalbumin, or lactoferrin.

In a third aspect, the present application provides a use of the *Bifidobacterium longum* subsp. *infantis* BI03 strain as described in the first aspect, or the microbial preparation as described in the second aspect in the preparation of a drug or a health product with the effect of preventing, alleviating or treating Parkinson's disease.

In a forth aspect, the present application provides a use of the the *Bifidobacterium longum* subsp. *infantis* BI03 strain as described in the first aspect, or the microbial preparation as described in the second aspect in the preparation of a drug for preventing, alleviating or treating motor deficit associated with Parkinson's disease.

In a fifth aspect, the present application provides a use of the the *Bifidobacterium longum* subsp. *infantis* BI03 strain as described in the first aspect, or the microbial preparation as described in the second aspect in the preparation of a drug for preventing, alleviating or treating neuroinflammatory injury associated with Parkinson's disease.

Compared with the prior art, the present application has the following beneficial effects.

In the present application, a new *Bifidobacterium longum* subsp. *infantis* for alleviating Parkinson's disease is isolated and deposited from fecal samples of healthy breastfed infants in Dali Bai Autonomous Prefecture, Yunnan Province, China, which is named as *Bifidobacterium longum* subsp. *infantis* BI03 strain. The *Bifidobacterium longum* subsp. *infantis* BI03 strain can significantly alleviate the symptoms of Parkinson's disease, specifically manifested in: (1) significantly alleviating Parkinson's disease-related dyskinesia and corticosterone elevation; (2) weakening the neuroinflammation associated with Parkinson's disease; (3) significantly promoting glutathione production and weakening brain oxidative stress damage. The present application provides new ideas for the development of new drugs to prevent or treat Parkinson's disease. In addition, *Bifidobacterium longum* subsp. *infantis* is a probiotic, it has high safety and not easy resistant when used in the preparation of products for preventing or treating Parkinson's disease.

Figure 1:
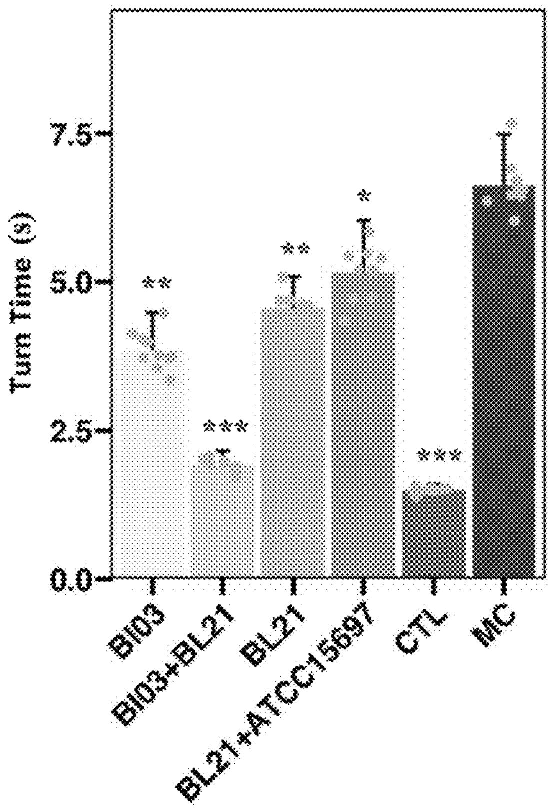
FIG. 1 is a graph showing the statistical results of the time required for each group of mice to turn completely downward (T-turn).

The data in FIGS. 1-14 is statistically analyzed using the ggplot2 function in R Programming Language (R 4.2.2). Compared with the model group (MC group), "*" stands for $p<0.05$, "" stands for $p<0.01$, "*" stands for $p<0.001$.

DETAILED DESCRIPTION

The technical solutions of the present application are further described below in terms of specific embodiments. It should be clear to those skilled in the art that the embodiments are merely used for a better understanding of the present application and should not be regarded as a specific limitation to the present application.

The following *Bifidobacterium longum* subsp. *infantis* BI03 strain is deposited in China General Microbiological Culture Collection Center on Mar. 7, 2022, with a deposit number of CGMCC No. 24473, and the deposit address is No. 3, Courtyard 1, West Beichen Road, Chaoyang District, Beijing, China.

The following *Bifidobacterium longum* BL21 strain is deposited in China General Microbiological Culture Collection Center on Jan. 27, 2015, with a deposit number of CGMCC No. 10452, and the deposit address is No. 3, Courtyard 1, West Beichen Road, Chaoyang District, Beijing, China.

The following MRS liquid medium includes, in terms of concentration: 10 g/L of peptone, 10 g/L of beef paste, 20 g/L of glucose, 2 g/L of sodium acetate, 5 g/L of yeast powder, 2 g/L of diammonium hydrogen citrate, 2.5 g/L of $K_2PO_4 \cdot 3H_2O$, 0.1 g/L of $MgSO_4 \cdot 7H_2O$, 0.05 g/L of $MnSO_4$, 1 mL/L of polysorbate 80, and 0.5 g/L of cysteine hydrochloride, dissolved in deionized water to make the total volume of the system to 1 L, sterilized and cooled for later use.

The preparation method for the bacterial suspension involves the following steps: the required strain is inoculated in the MRS liquid culture medium, cultured at 37° C. for 18 h for activation, the activation is performed twice continuously to obtain an activation solution; the activation solution is inoculated in the MRS liquid culture medium at an inoculate dosage of 5% (v/v), cultured at 37° C. for 24 h to obtain a bacterial solution; the bacterial solution is centrifuged at a rotational speed of 8000 g for 15 min, and then the bacterial pellet are resuspended by PBS to obtain the bacterial suspension.

Example 1

In this example, a strain of *Bifidobacterium longum* subsp. *infantis* for alleviating Parkinson's disease is screened, and the steps are as follows.

(1) A fecal sample of healthy breastfed infants in Dali Bai Autonomous Prefecture, Yunnan Province, China, was diluted 10-fold gradient with 0.9% normal saline for 3 times, coated on an MRS solid medium (reagents were purchased from Hope Bio), cultured at 37° C. for 48 h, and then colonies with different morphologies were picked out and streaked on the surface of the MRS solid medium for purification, single colonies were picked out and cultured with MRS liquid medium at 37° C. for expanding, and then preserved with a 30% mass concentration of glycerol.

(2) In vitro physiological properties tests in view of the several preserved strains were performed, and a single strain with the best gastrointestinal fluid tolerance (artificial simulation), HT-29 cell adhesion ability, bacteriostatic ability and functional oligosaccharide utilization ability was screened out. The details were as follows.

(2.1) Test on Gastrointestinal Fluid Tolerance

Artificial simulation of gastric fluid: 0.5% NaCl solution was prepared, added with 0.3% pepsin, and adjusted the pH to 2.5 with 1 mol/L HCl, after fully dissolved, the solution was subjected to filter with a microporous filter membrane of 0.22 m to remove the bacteria for later use.

Artificial simulation intestinal fluid: 0.5% NaCl solution was prepared, added with 0.1% trypsin, and adjusted the pH to 8.0 with 0.1 mol/L NaOH, after fully dissolved, the solution was subjected to filter with a microporous filter membrane of 0.22 m to remove the bacteria for later use.

The strains to be selected were anaerobically cultured in artificial gastric fluid or intestinal fluid for 3 h. The digested fluids at 0 h and 3 h were taken for viable bacteria counts and the survival rate was calculated. The survival rate of the strain (%)=B/A×100%, wherein A represents the viable bacteria count at 0 h (CFU/mL) and B represents the viable bacteria count at 3 h (CFU/mL).

(2.2) Test on HT-29 Cell Adhesion Ability

The concentration of digested HT-29 cells was adjusted to $1 \times 10^5$/mL, 1 mL of the solution was taken to inoculate into each well of a 12-well cell culture plate, incubated in an incubator at 5% $CO_2$ concentration until the cells grew to a monolayer, washed twice with sterile PBS, and one well was digested with trypsin, cells of which were counted with a hemocytometer; other wells were added with 1 mL of a suspension of candidate bacterial strains separately (the concentration of the bacterial suspension was adjusted to $10^8$ CFU/mL), incubated at 37° C. for 2 h in a 5% $CO_2$ incubator, washed the cells with sterile PBS for 5 times to remove non-adhered bacterial suspension, and added with 0.2 mL of trypticase-EDTA buffer into each well to digest the cells for 5 min, then added 0.8 mL of PBS to blow uniformly after digestion, and the bacterial solution was taken to dilute and count viable bacteria.

(2.3) Test on Bacteriostatic Ability

The Oxford cup method was used to test the inhibition ability to pathogenic bacteria. The pathogenic strain of *Escherichia coli* was inoculated in liquid beef paste-peptone medium and incubated overnight at 37° C., 250 rpm, on a constant temperature shaker to prepare pathogenic bacterial suspension. The MRS solid medium was cooled to about 55° C., mixed with the pathogenic bacteria suspension according to a certain proportion to make the viable count of the pathogenic bacteria in the system in an order of 106 CFU/mL, and then the mixture was quickly poured into a plate with an Oxford cup pre-placed, and moved the Oxford cup out after the medium was cooled and solidified, and injected 200 L of bacterial solution of the to-be-tested strains into each well, then the petri dish was lightly covered and placed in a 37° C. constant-temperature incubator in an upright position, observed and measured the diameter of the bacteriostatic circle by a vernier caliper after cultivated for a suitable period of time. The larger the bacteriostatic circle, the stronger the bacteriostatic ability.

(2.4) Test on Utilization Ability to Functional Oligosaccharide

Sugar-free medium: 1% peptone, 1% beef paste, 0.5% yeast extract, 0.2% diammonium hydrogen citrate, 0.2% $K_2HPO_4$, 0.058% $MgSO_4$, 0.019% $MnSO_4$, 0.10 Tween-80, 0.1% L-cysteine hydrochloride. The xylo-oligosaccharide, inulin, oligofructose, and oligogalactose were purchased from Quantum Hi-Tech (China) Biological Co., Ltd, and the xylo-oligosaccharide was purchased from Shandong Longlive Biotech. Co., Ltd.

The xylo-oligosaccharide, inulin, oligofructose and oligogalactose were added to the above sugar-free medium at 2% to obtain the medium containing oligosaccharides as carbon source. The strain-to-be-selected was inoculated into the oligosaccharide-containing medium, and incubated at a constant temperature of 37° C. for 12 h. The GD 600 absorbance was measured to determine the utilization ability of the strain to functional oligosaccharide.

Example 2

In this example, cell morphology, physicochemical experiments and molecular biology identification are performed on the strain selected by Example 1, and the details are as follows.

(1) The results of cell morphology and physicochemical experiments are shown in Table 1.

TABLE 1

| Test item | Result | Test item | Result | Test item | Result |
|---|---|---|---|---|---|
| Gram staining | Positive | Catalase | – | Oxidase | – |
| Cellular morphology | Multi-shaped rod-shape | | | | |
| Carbohydrates produce acid (API 50CH) | | | | | |
| Glycerol | – | Inositol | – | Inulin | – |
| Erythritol | – | Mannitol | – | Melezitose | – |
| D-arabinose | – | Sorbitol | – | Raffinose | + |
| L-arabinose | – | α-methyl-D-mannoside | – | Starch | – |
| D-ribose | + | α-methyl-D-glucoside | – | Glycogen | – |
| D-xylose | + | N-acetyl-glucosamine | + | Xylitol | – |
| L-xylose | – | Amygdalin | – | Gentiobiose | – |
| Adonitol | – | Arbutin | – | D-turanose | – |
| β-methyl-D-xyloside | – | Esculin | – | D-lyxose | – |
| D-galactose | + | Salicin | – | D-tagatose | – |
| D-glucose | + | Cellobiose | – | D-fucose | – |
| D-fructose | + | Maltose | + | L-fucose | – |
| D-mannose | + | Lactose | + | D-arabite | – |
| L-sorbose | – | Melibiose | + | L-arabite | – |
| L-rhamnose | – | Sucrose | + | Gluconate | – |
| Melampyrite | – | Trehalose | – | 2-Keto-gluconate | – |

(2) The sequence determination result of 16S rRNA gene is shown in SEQ ID No: 1.

```
SEQ ID No: 1:
ACAAGGGGTTAGGCCACCGGCTTCGGGTGCTGCCCACTTTCATGACTTG

ACGGGCGGTGTGTACAAGGCCCGGGAACGCATTCACCGCGACGTTGCTG

ATTCGCGATTACTAGCGACTCCGCCTTCACGCAGTCGAGTTGCAGACTG

CGATCCGAACTGAGACCGGTTTTCAGGGATCCGCTCCGCGTCGCCGCGT

CGCATCCCGTTGTACCGGCCATTGTAGCATGCGTGAAGCCCTGGACGTA

AGGGGCATGATGATCTGACGTCATCCCCACCTTCCTCCGAGTTAACCCC

GGCGGTCCCCCGTGAGTTCCCGGCACAATCCGCTGGCAACACGGGGCGA

GGGTTGCGCTCGTTGCGGGACTTAACCCAACATCTCACGACACGAGCTG

ACGACGACCATGCACCACCTGTGAACCCGCCCCGAAGGGAAACCCCATC

TCTGGGATCGTCGGGAACATGTCAAGCCCAGGTAAGGTTCTTCGCGTTG

CATCGAATTAATCCGCATGCTCCGCCGCTTGTGCGGGCCCCCGTCAATT

TCTTTGAGTTTTAGCCTTGCGGCCGTACTCCCCAGGCGGGATGCTTAAC

GCGTTAGCTCCGACACGGAACCCGTGGAACGGGCCCCACATCCAGCATC

CACCGTTTACGGCGTGGACTACCAGGGTATCTAATCCTGTTCGCTCCCC

ACGCTTTCGCTCCTCAGCGTCAGTAACGGCCCAGAGACCTGCCTTCGCC

ATTGGTGTTCTTCCCGATATCTACACATTCCACCGTTACACCGGGAATT

CCAGTCTCCCCTACCGCACTCAAGCCCGCCCGTACCCGGCGCGGATCCA

CCGTTAAGCGATGGACTTTCACACCGGACGCGACGAACCGCCTACGAGC

CCTTTACGCCCAATAATTCCGGATAACGCTTGCACCCTACGTATTACCG

CGGCTGCTGGCACGTAGTTAGCCGGTGCTTATTCAACGGGTAAACTCAC
```

-continued

```
TCACGCTTGCTCCCCGATAAAAGAGGTTTACAACCCGAAGGCCTCCATC

CCTCACGCGGCGTCGCTGCATCAGGCTTGCGCCCATTGTGCAATATTCC

CCACTGCTGCCTCCCGTAGGAGTCTGGGCCGTATCTCAGTCCCAATGTG

GCCGGTCGCCCTCTCAGGCCGGCTACCCGTCGAAGCCACGGTGGGCCGT

TACCCCGCCGTCAAGCTGATAGGACGCGACCCCATCCCATACCGCGAAA

GCTTTCCCAGAAGACCATGCGATCAACTGGAACATCCGGCATTACCACC

CGTTTCCAGGAGCTATTCCGGTGTATGGGGCAGGTCGGTCACGCATTAC

TCACCCGTTCGCCACTCTCACCACCAAGCAAGCTTGATGGATCCCGTTC

GACT.
```

(3) The sequence determination result of tuf gene is shown in SEQ ID No: 2.

```
SEQ ID No: 2:
CGCACAGCGAAGGTCAGGCCTTCCTCCATGGCGATGGGCTGAATCAGCT

CAACGGTGAAGGTGGCGTGGTCGCCGGGCTGAACCATCTCGACGCCTTC

CGGCAGCTCGATGACGCCGGTGACGTCGGTGGTGCGGAAGTAGAACTGC

GGACGGTAGTTGGAGAAGAACGGCGAGTGACGGCCGCCCTCGTCCTTGG

TCAGCACGTAGACTTCGCCCTCGAACTTGGTGTGCGGGGTGACGGAGCC

TGGCTTGGCCACGACCTGACCGCGCTCGACATCCTCACGGCCGAGGCCA

CGCAGCAGCAGACCGGTGTTATCGCCAGCCTCGCAGGCGTCCATGGTCT

TGTGGAAGGTCTCGATGGAGGTGACGGTGGTGGTCTGGGTCGGACGGAT

GCCGACGATCTCGACCGGGGTGTTGACGGCCAGCTGGCCACGCTCGACA

CGACCGGTGACGACGGTACCACGGCCGGAGATGGTGAAGACGTCCTCGA

TCGGCATCAGGAACGGCTTGTCCAGGTCGTGAACCGGGGTCGGGATGTA

GAGCGTCGTCGTGCAGGGCGCCGTAGGCGGAGGTGTGGATGACCGGGCA

GGTCATCGACGGCGGCCATGAGGTCCTTGACGGACTGGACCCACTTCTC

GTGGTCCGTCGCGATCGAAGCCGTTCTCGTCGAGGAGGTCACGGACCTC

TTCTTCGACGAGCTCGATGAGCTCTTCATCGTCGACCATGTCGCACTTG

TTGAGGGCGACAGGATCTTCGGGACGCCGACCTGACGGGCGAGCAGCAC

GTGCTCGCGGGTCTGGGCCATCGGGCCGTCGGTGGCGGCCACAACAGGG

ATGGCCGCCATCCATCTGGGCAGCACCGGTGATCATGTTCTTCACGAAG

TCGGCGTGGCCCGGGCAGTCGACGTGAGCGTAGTGACGCTTCTCGGTCT

GGTACTCGATGTGGG.
```

The sequences obtained by sequencing were subjected to nucleic acid sequence alignment in GeneBank, and the results showed that the strain was indeed the *Bifidobacterium longum* subsp. *infantis*.

Example 3

This example verifies the effects of the *Bifidobacterium longum* subsp. *infantis* BI03 strain on serum corticosterone, brain oxidative stress markers, motor behavioral ability, brain neurotransmitter levels, and neuroinflammation in mice modeled for Parkinson's disease, and the steps are as follows.

(1) Test animals: 48 16-week-old SAMP8 male adult mice (22±2 g) were adaptively fed with regular feed for one week (free to diet and water) in an animal house (room temperature: 23-25° C., humidity: 50-70%, lighting for 10±0.5 h).

(2) Animal grouping: after adaptive feeding, mice were randomly assigned to 6 groups: control group (CTL group), model group (MC group), BI03 group, BL21 group, BI03 and BL21 combined group (combined group 1), ATCC 15697 and BL21 combined group (combined group 2), with 8 mice in each group.

(3) Intervention Method

In all groups of mice except the control group, MPTP (1-methyl-4-phenyl-1,2,3,6-tetrahydropyridine, 30 mg/kg, Sigma-Aldrich) was given by gavage for 4 consecutive weeks; the probiotic intervention groups (BI03 group, BL21 group, combined group 1, and combined group 2) were simultaneously gavaged with $1\times10^9$ CFU/day of the bacterial solution, respectively (the ratio of viable bacteria count of the BI03 to BL21 in combined group 1 was 3:1, the ratio of viable bacteria count of the ATCC 15697 to BL21 in combined group 2 was 3:1), while the control group was gavaged with 200 L/day of saline for 4 consecutive weeks.

(4) Effect on Motor Behaviour

After intervention, the motility of the mice was assessed by 3 behavioral tests: the pole test (PT), narrow-beam test (NBT) and rotarod test (RTR). All mice received behavioral training once daily from days 20-22, and the behavioral test was performed on day 29 (24 h after the last MPTP injection). Both PT and NBT were videotaped and the video file names were converted to random numeric codes and analyzed by three researchers blinded to the treatment conditions. The specific operations were carried out by conventional experimental methods in prior art.

Figure 2:
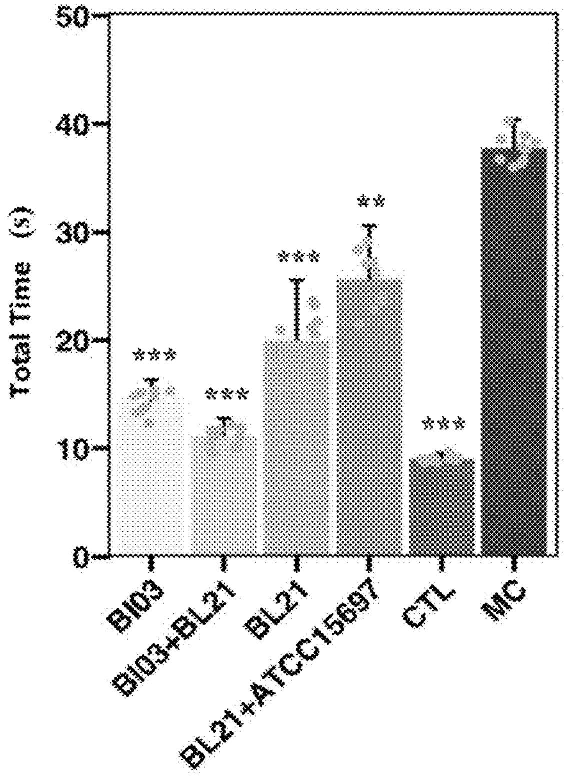
FIG. 2 is a graph showing the statistical results of the time required for each group of mice to descend to the floor (T-total).

(4.1) PT (used to assess agility and sensorimotor disturbance): a vertically placed metal pole with a length of about 50 cm and a diameter of 1 cm was prepared. On each training day, the mice were first placed in the pole cage to familiarize themselves with the environment, and then placed the mice head up on the pole 15 cm from the bottom of the cage three times, followed by three training sessions on the pole 30 cm and 50 cm above the cage floor. On the day of the test, each mouse was placed head up on top of the pole, and the time required to turn completely downward (T-turn) and the time required to descend to the floor (T-total) were recorded. If the mouse fell or jumped off the pole within 60 s, the test was repeated. If the mouse was unable to turn its head down or kept falling off the pole, the time of the T-turn and T-total was recorded as 60 s. Each mouse was tested 3 times (test interval of 1 min) and the average time was taken. The results are shown in FIGS. 1 and 2.

Figure 3:
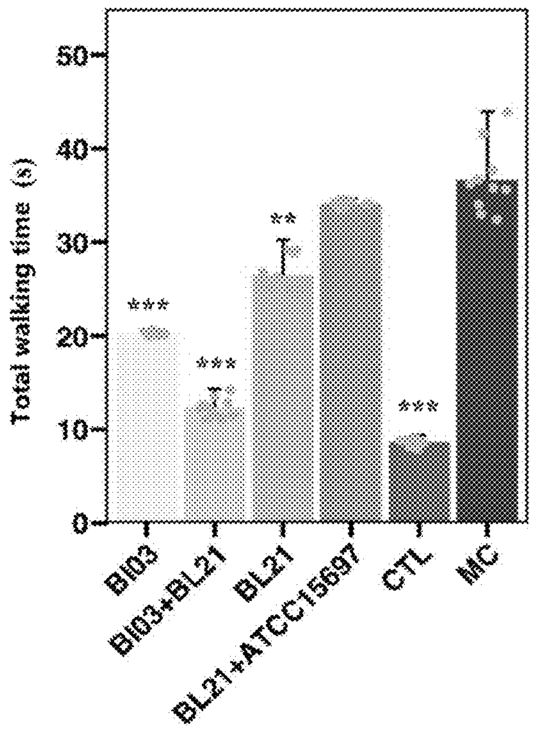
FIG. 3 is a graph showing the statistical results of the time required for each group of mice to cross the beam and enter the finish line.

(4.2) NBT (assesses motor coordination and balance): a slender strip of wood was prepared with a length of 50 cm and a width of 0.8 cm. The beam was mounted on two poles with a height of 50 cm from the tabletop. A black box was placed at one end of the beam as the endpoint, and the black box was filled with rat feed to attract mice. On each training day, the mice were placed in a black box for 5 min to familiarize themselves with the environment, and then placed on the beam 5 cm away from the box and trained to walk towards the case 3 times, followed with balance beam walk trainings of 15 cm, 30 cm and 50 cm. On the day of the test, each mouse was tested three times (test interval of 1 min). Recorded the time required to pass through the beam and enter endpoint, until completion or up to 60 s. If the mouse fell midway or returned to the starting point, the test was repeated. If the mouse was unable to arrive at the endpoint within 60 s or kept falling off the beam, the total time was recorded as 60 s. The average time of the 3 experiments was taken, and the result is shown in FIG. 3.

Figure 4:
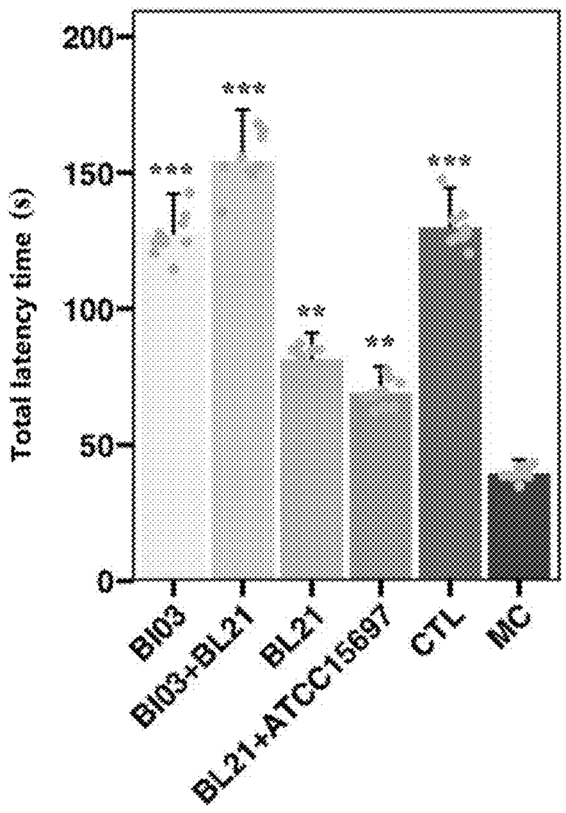
FIG. 4 is a graph showing the statistical results of the latency time of falling for each group of mice.

(4.3) RTR (assesses motor coordination): RT-01 mouse rotarod containing an automatic timer and a drop sensor was used during the training period and the formal testing. All mice were first subjected to training at a rotation speed of 10 rpm for 180 s×3 times on day 20, followed by a rotation speed of 20 rpm on day 21 and a rotation speed of 30 rpm on day 22. On the test day, each mouse was tested at a rotation speed of 30 rpm for 180 s×3 times (test interval of 1 min), the latency time of the fall was recorded, and the average time was taken. The result is shown in FIG. 4.

From the results of FIGS. 1-4, it can be seen that compared with the CTL group, the mice in the MC group showed a significant increase in T-turn and T-total on PT, that is, Parkinson's disease mice showed dyskinesia and balance problems, resulting in a longer time to slide the pole; the total walking time significantly increased on NBT, indicating that Parkinson's disease mice exhibited unstable and uncoordinated gait, making them prone to errors; and the residence time on RTR was significantly reduced, indicating that Parkinson's disease mice exhibited balance disorders and lack of coordination, making them difficult to maintain balance on rotating cylinders. After the intervention of BI03 strain, the motor deficits on PT, NBT and RTR of Parkinson's disease mice were significantly weakened, indicating that the BI03 strain treatment could alleviate the motor deficits in Parkinson's disease mice. In particular, the effect can be more obvious when the probiotic BI03 is combined with BL21 (note: compared with the model group *p<0.001, p<0.01, *p<0.05).

After behavioral tests on day 29, all mice were anesthetized by intraperitoneal injection of 10% chloral hydrate (2 mL/kg) and subjected to cervical dislocation, and their brains and blood were collected.

(5) Detection of Corticosterone in Serum

Figure 5:
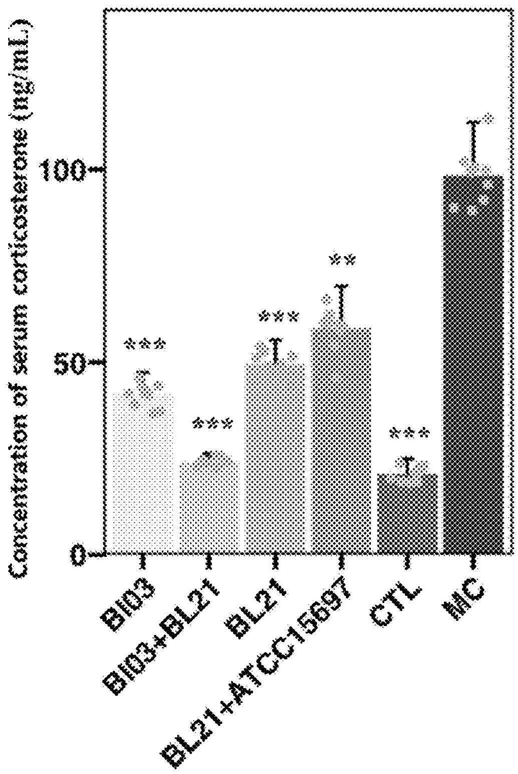
FIG. 5 is a graph showing the statistical results of serum corticosterone levels for each group of mice.

Commercial CORT EIAkit was used to measure corticosterone concentration in serum in each group of mice (product number: K014-H5W, Arbor Assays), and analyzation was carried out according to the manufacturer's instructions. The result is shown in FIG. 5, it can be seen that compared with the CTL group, the serum corticosterone content of mice in the MC group was significantly increased, which may be related to the inflammatory response of Parkinson's disease. Inflammation is an important feature of Parkinson's disease, which may be related to damage to nerve cells and the release of inflammatory mediators that can stimulate the adrenal gland to secrete more corticosteroids. Under the intervention of the probiotic, the serum corticosterone levels in all groups decreased, wherein the degree of reversal is most pronounced when the BI03 and the BL21 are worked together (note: compared with the model group, *p<0.001, p<0.01, *p<0.05).

(6) Detection of tumor necrosis factors TNF-α, IL-1β, and IL-6 in serum

Figure 6:
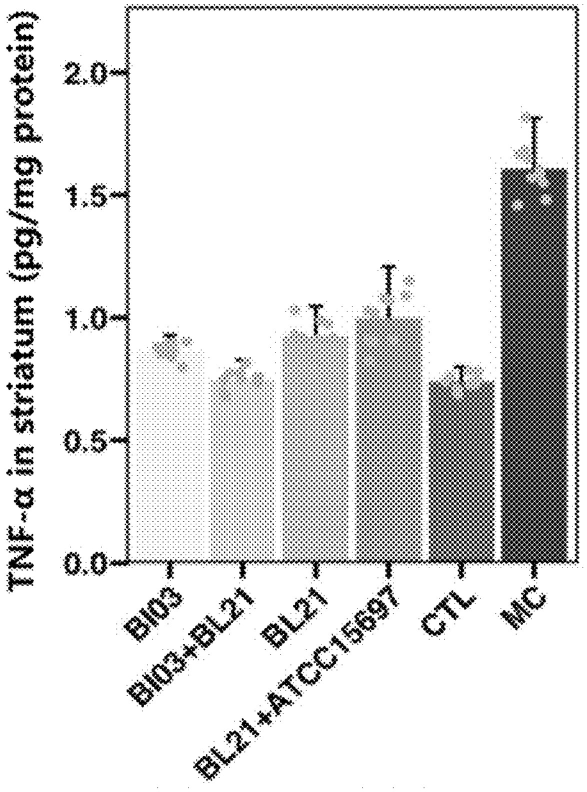
FIG. 6 is a graph showing the statistical results of serum tumor necrosis factor TNF-α levels for each group of mice.
Figure 7:
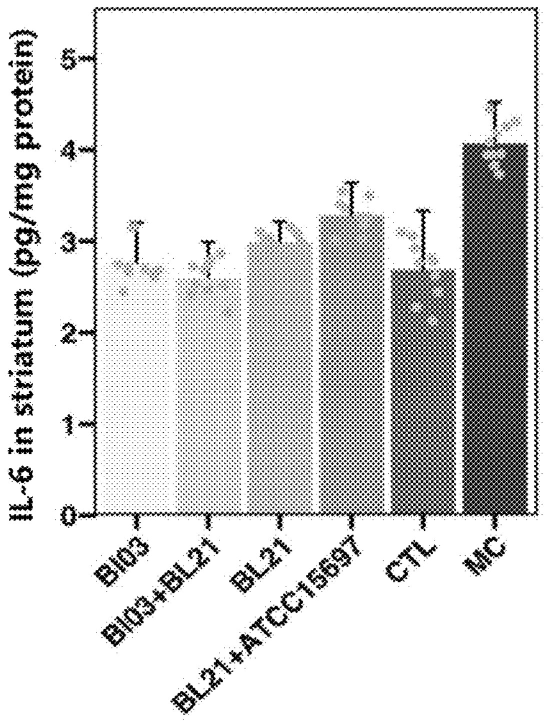
FIG. 7 is a graph showing the statistical results of serum tumor necrosis factor IL-6 levels for each group of mice.
Figure 8:
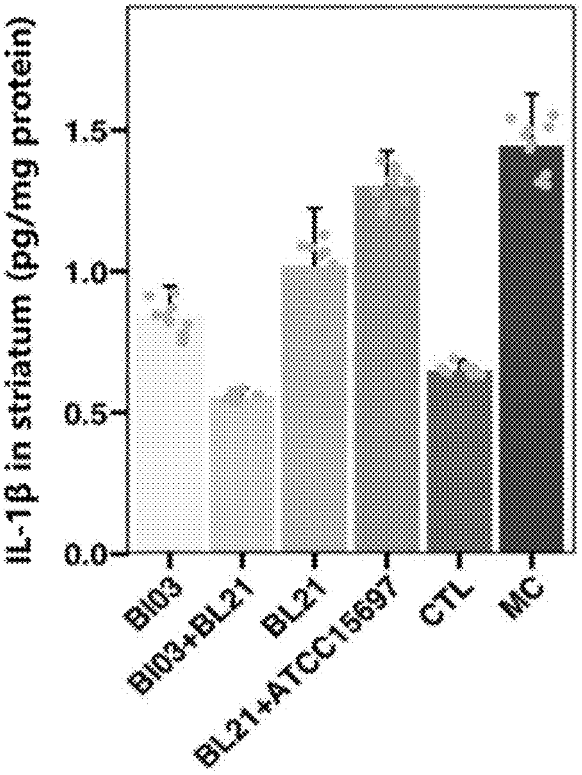
FIG. 8 is a graph showing the statistical results of serum tumor necrosis factor IL-1β levels for each group of mice.

An ELISA kit (Shanghai Enzyme-linked Biotechnology Co., Ltd.) was used to detect the levels of serum tumor necrosis factors TNF-α, IL-1β, and IL-6 in each group of mice. The results are shown in FIGS. 6-8. It can be seen from the figures that compared with the CTL group, Parkinson's disease mice have increased levels of TNF-α, IL-1β, and IL-6 in the striatum of brain. The intake of the BI03 strain successfully alleviated the increase of levels of TNF-α, IL-1β, and IL-6 in the striatum in Parkinson's disease mice, and the effect of the BI03 combined with the BL21 was more prominent. That is, the probiotic may reduce the damage and degeneration of neurons by inflammation through reducing the levels of pro-inflammatory cytokines in striatal tissue of brain, thereby may help to alleviate symptoms in Parkinson's disease mice (note: compared to the model group *p<0.001, p<0.01, *p<0.05).

(7) Detection of Markers of Cerebral Oxidative Stress

Figure 9:
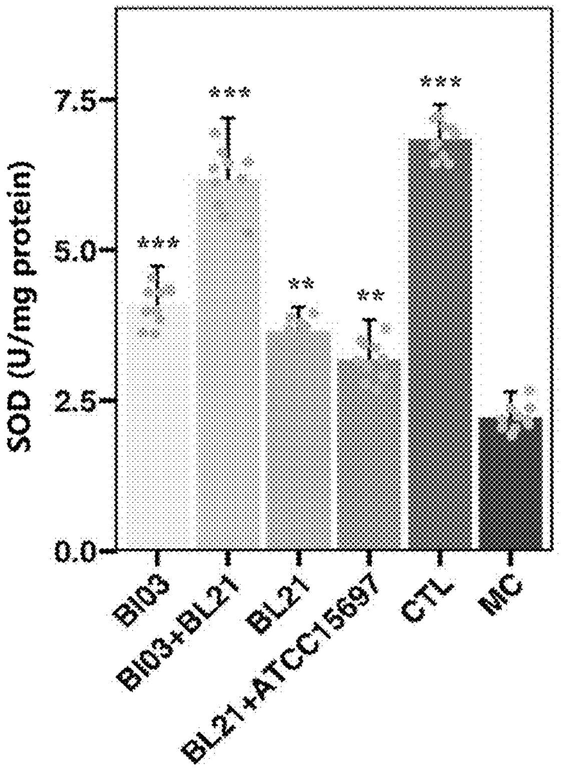
FIG. 9 is a graph showing the statistical results of the levels of superoxide dismutase (SOD), a marker of oxidative stress in the brains for each group of mice.
Figure 10:
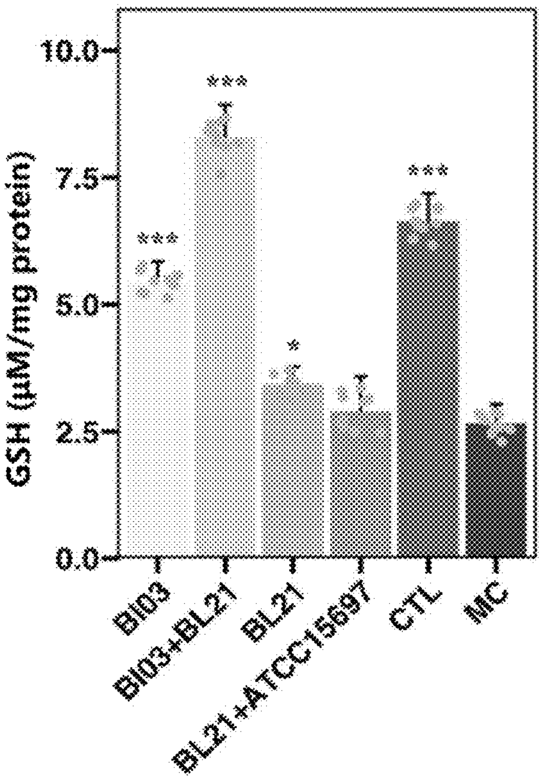
FIG. 10 is a graph showing the statistical results of the levels of glutathione (GSH), a marker of oxidative stress in the brains for each group of mice.
Figure 11:
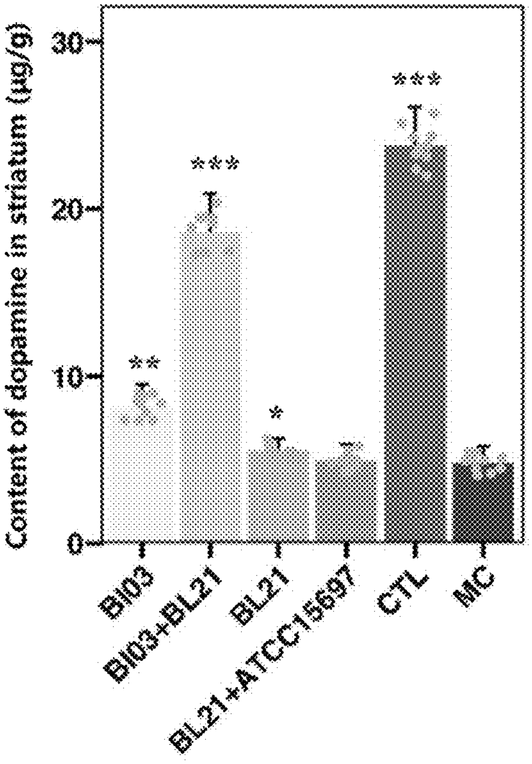
FIG. 11 is a graph showing the statistical results of dopamine levels in striatum for each group of mice.
Figure 12:
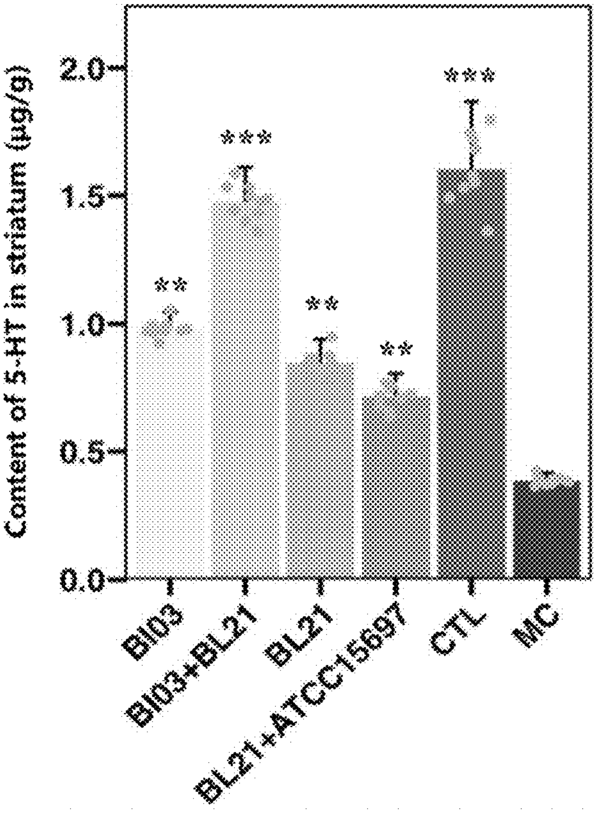
FIG. 12 is a graph showing the statistical results of 5-HT levels in the striatum for each group of mice.
Figure 13:
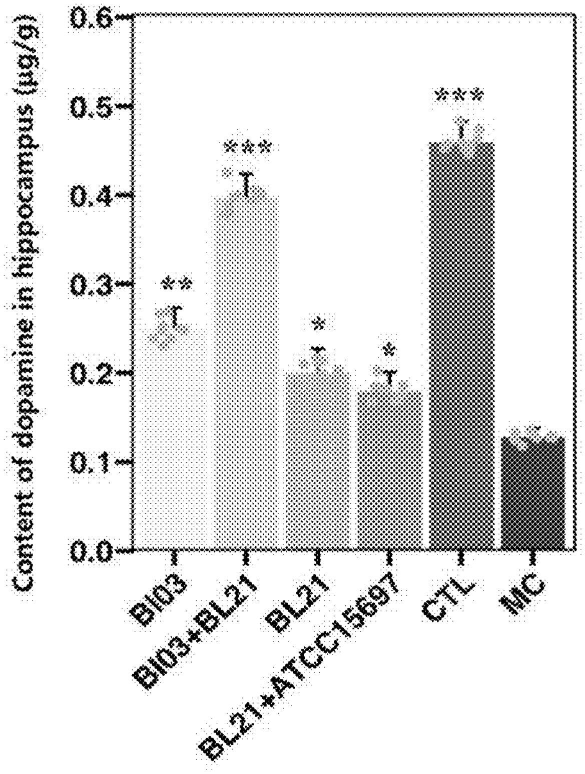
FIG. 13 is a graph showing the statistical results of dopamine levels in hippocampus for each group of mice.
Figure 14:
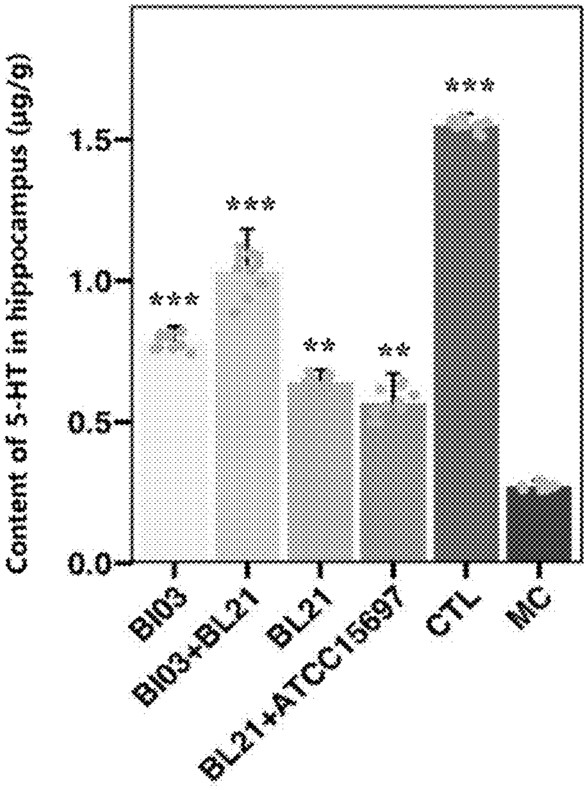
FIG. 14 is a graph showing the statistical results of 5-HT level in hippocampus for each group of mice.

A kit was used to detect the levels of superoxide dismutase (SOD) and glutathione (GSH) according to the antioxidant activity. The brain tissue (striatum) of each group of mice was treated with ultrasound in PBS buffer. After centrifugation, the supernatant was collected and analyzed using a testing kit according to the protocols of the kit. Antioxidant levels in mouse brain tissue were estimated based on antioxidant standard activity. The results are shown in FIGS. 9 and 10, and it can be seen from the figures that by measuring the levels of antioxidant activity in the striatum region of mice, we found that the levels and activity of SOD and GSH in the striatal region of mice in the MC group were significantly reduced compared with the CTL group. SOD and GSH are important intracellular antioxidants that play a crucial role in protecting cells from oxidative stress damage. The nerve cells in the striatum of Parkinson's disease mice may be damaged, leading to functional abnormalities and death of cells, thereby triggering an inflammatory response, and promoting the release of inflammatory mediators.

The inflammatory response can lead to an increase in the consumption of SOD and GSH, resulting in a decrease in the levels of SOD and GSH. The intervention of the probiotic can effectively reverse the trend, wherein the reversal trend of BI03 group is significant, and the reversal trend of the BI03 and BL21 combined group is most significant (note: compared with the model group, *p<0.001, p<0.01, *p<0.05).

(8) Detection of Level of Neurotransmitters in Brain

The striatum and hippocampus samples on both sides of the mice in each group were homogenized, and centrifuged at 12000 g at 4° C. for 10 min. The supernatant was filtered with a membrane of 0.22 m, and the filtrate was used for HPLC-MS detection. In the HPLC section, a Thermo Vanquish high performance liquid chromatography system from Thermo Fisher Scientific was used, and an ACQUITY UPLC HSST3 chromatographic column (2.1×150 mm, 1.8 μm) from Waters was used. The flow rate was set to 0.25 mL/min, the column temperature was 40° C., and the injection volume was 2 μL. In the mass spectrometry section, a Thermo Q Exactive Focus mass detector from Thermo Fisher Scientific was used and data acquisition was performed using an electrospray ion source (ESI) in positive and negative ion modes, respectively.

Parkinson's disease is a degenerative disease of the nervous system, one of its characteristics is the decreased of dopamine and 5-HT levels in the bilateral striatum and hippocampus. From FIGS. 11-14, it can be seen that compared with the CTL group, the contents of 5-HT and dopamine in the bilateral striatum and hippocampus of mice decreased in the MC group. 5-HT is a neurotransmitter that regulates mood and cognitive function. Parkinson's disease is often accompanied by a decrease in 5-HT levels, leading to the appearance of emotional and cognitive problems. Dopamine is an important neurotransmitter that is essential for motor regulation. The loss of dopamine neurons in Parkinson's disease mice leads to a decrease in dopamine levels, which in turn triggers symptoms such as dyskinesia. After intervention with the probiotic, the levels of neurotransmitters have a slightly increase. The increase in dopamine and 5-HT levels was more significant in the BI03 and BL21 combined group (note: compared with the model group, *p<0.001, p<0.01, *p<0.05).

The applicant declares that the present application illustrates a *Bifidobacterium longum* subsp. *infantis* for alleviating Parkinson's disease and use thereof of the present application by the above examples, but the present application is not limited to the above examples, that is, the present application does not necessarily rely on the above examples to be implemented. Those skilled in the art should understand that any improvements of the present application, the equivalent substitution of each raw material, the addition of auxiliary ingredients, and the selection of specific methods shall fall within the protection scope and disclosure scope of the present application.

The above describes in detail the preferred embodiments of the present application. However, the present application is not limited to the specific details in the above embodiments, and various simple variations of the technical solutions of the present application can be made within the scope of the technical conception of the present application, all of these simple variations shall fall within the protection scope of the present application.

It is also to be noted that the various specific technical features described in the above specific embodiments may be combined in any suitable manners without contradiction, and in order to avoid unnecessary repetition, the various possible combinations are not described separately in the present application.

What is claimed is:

1. A microbial preparation for alleviating symptoms associated with Parkinson's disease, comprising the *Bifidobacterium longum* subsp. *infantis* which is named *Bifidobacterium longum* subsp. *infantis* BI03 strain deposited Mar. 7, 2022 with the deposit number of CGMCC No. 24473 and the *Bifidobacterium longum* subsp. *infantis* which is named *Bifidobacterium longum* subsp. *infantis* BL21 strain deposited Jan. 27, 2015 with the deposit number of CGMCC No. 10452; wherein the viable bacteria count ratio of the *Bifidobacterium longum* subsp. *infantis* BI03 to the *Bifidobacterium longum* subsp. *infantis* BL21 is (2-4): 1; and wherein the viable cell count of the *Bifidobacterium longum* subsp. *infantis* BI03 is not less than $1\times10^9$ CFU/mL or $1\times10^9$ CFU/g; and wherein the microbial preparation is in a dosage form selected from the group consisting of a lyophilized powder, a capsule, a tablet and a granule.

2. The microbial preparation for alleviating symptoms associated with Parkinson's disease according to claim 1, wherein the microbial preparation further comprises a protectant and/or an auxiliary additive.

3. The microbial preparation for alleviating symptoms associated with Parkinson's disease according to claim 2, wherein the protectant is selected from any one or a combination of at least two of skimmed milk, gelatin, maltodextrin, Arabic gum, dextran, sodium algae, polyvinyl pyrrolidone, sucrose, lactose, trehalose, sorbitol or xylitol.

4. The microbial preparation for alleviating symptoms associated with Parkinson's disease according to claim 2, wherein the auxiliary additive is selected from any one or a combination of at least two of resistant dextrin, oligofructose, oligogalactose, oligoxylose, iso-malto-oligosaccharide, soybean oligosaccharide, inulin, *Spirulina, Arthrospira, Coriolus versicolor* polysaccharide, stachyose, polyglucose, α-lactalbumin, or lactoferrin.

5. A method for alleviating symptoms associated with Parkinson's disease comprising administering an effective amount of the microbial preparation of claim 1 to a subject in need thereof.

* * * * *

SEQUENCE LISTING

```
Sequence total quantity: 2
SEQ ID NO: 1            moltype = DNA  length = 1376
FEATURE                 Location/Qualifiers
source                  1..1376
                        mol_type = other DNA
                        organism = synthetic construct
SEQUENCE: 1
acaaggggtt aggccaccgg cttcgggtgc tgcccacttt catgacttga cgggcggtgt  60
gtacaaggcc cgggaacgca ttcaccgcga cgttgctgat tcgcgattac tagcgactcc  120
gccttcacgc agtcgagttg cagactgcga tccgaactga gaccggtttt cagggatccg  180
ctccgcgtcg ccgcgtcgca tcccgttgta ccggccattg tagcatgcgt gaagccctgg  240
acgtaagggg catgatgatc tgacgtcatc cccaccttcc tccgagttaa ccccggcggt  300
cccccgtgag ttcccggcac aatccgctgg caacacgggg cgagggttgc gctcgttgcg  360
ggacttaacc caacatctca cgacacgagc tgacgacgac catgcaccac ctgtgaaccc  420
gccccgaagg gaaaccccat ctctgggatc gtcgggaaca tgtcaagccc aggtaaggtt  480
cttcgcgttg catcgaatta atccgcatgc tccgccgctt gtgcgggccc ccgtcaattt  540
ctttgagttt tagccttgcg gccgtactcc ccaggcggga tgcttaacgc gttagctccg  600
acacggaacc cgtggaacgg gccccacatc cagcatccac cgtttacggc gtggactacc  660
```

-continued

```
agggtatcta atcctgttcg ctccccacgc tttcgctcct cagcgtcagt aacggcccag  720
agacctgcct tcgccattgg tgttcttccc gatatctaca cattccaccg ttacaccggg  780
aattccagtc tcccctaccg cactcaagcc cgcccgtacc cggcgcggat ccaccgttaa  840
gcgatggact ttcacaccgg acgcgacgaa ccgcctacga gccctttacg cccaataatt  900
ccggataacg cttgcaccct acgtattacc gcggctgctg gcacgtagtt agccggtgct  960
tattcaacgg gtaaactcac tcacgcttgc tccccgataa aagaggttta caacccgaag  1020
gcctccatcc ctcacgcggc gtcgctgcat caggcttgcg cccattgtgc aatattcccc  1080
actgctgcct cccgtaggag tctgggccgt atctcagtcc caatgtggcc ggtcgccctc  1140
tcaggccggc tacccgtcga agccacggtg ggccgttacc ccgccgtcaa gctgatagga  1200
cgcgaccccca tcccataccg cgaaagcttt cccagaagac catgcgatca actggaacat  1260
ccggcattac cacccgtttc caggagctat tccggtgtat ggggcaggtc ggtcacgcat  1320
tactcacccg ttcgccactc tcaccaccaa gcaagcttga tggatcccgt tcgact      1376

SEQ ID NO: 2           moltype = DNA  length = 946
FEATURE                Location/Qualifiers
source                 1..946
                       mol_type = other DNA
                       organism = synthetic construct
SEQUENCE: 2
cgcacagcga aggtcaggcc ttcctccatg gcgatgggct gaatcagctc aacggtgaag  60
gtggcgtggt cgccgggctg aaccatctcg acgccttccg gcagctcgat gacgccggtg  120
acgtcggtgg tgcggaagta gaactgcgga cggtagttgg agaagaacgg cgagtgacgg  180
ccgccctcgt ccttggtcag cacgtagact tcgccctcga acttggtgtg cggggtgacg  240
gagcctggct tggccacgac ctgaccgcgc tcgacatcct cacggccgag gccacgcagc  300
agcagaccgg tgttatcgcc agcctcgcag gcgtccatgg tcttgtggaa ggtctcgatg  360
gaggtgacgg tggtggtctg ggtcggacgg atgccgacga tctcgaccgg ggtgttgacg  420
gccagctggc cacgctcgac acgaccggtg acgacggtac cacggccgga gatggtgaag  480
acgtcctcga tcggcatcag gaacggcttg tccaggtcgt gaaccggggt cgggatgtag  540
tcatcgacgg cggccatgag gtccttgacg gactggaccc acttctcgtg gtccggagcg  600
tcgtcgtgca gggcgccgta ggcggaggtg tggatgaccg ggcagtcgcg atcgaagccg  660
ttctcgtcga ggaggtcacg gacctcttct tcgacgagct cgatgagctc ttcatcgtcg  720
accatgtcgc acttgttgag ggcgacagga tcttcgggac gccgacctga cgggcgagca  780
gcacgtgctc gcgggtctgg gccatcgggc cgtcggtggc ggccacaaca gggatggccg  840
ccatccatct gggcagcacc ggtgatcatg ttcttcacga agtcggcgtg gcccgggcag  900
tcgacgtgag cgtagtgacg cttctcggtc tggtactcga tgtggg                 946
```